United States Patent [19]

Yamanaka et al.

[11] 4,175,130
[45] Nov. 20, 1979

[54] OXAZOLE- AND THIAZOLE-ALKANOIC ACID COMPOUNDS

[75] Inventors: Tsutomu Yamanaka; Hiroshi Yasuda, both of Oita; Kunio Osuga, Yoshitomi, all of Japan

[73] Assignee: Yoshitomi Pharmaceutical Industries, Ltd., Osaka, Japan

[21] Appl. No.: 889,073

[22] Filed: Mar. 22, 1978

[30] Foreign Application Priority Data

Mar. 25, 1977 [JP] Japan .................. 52-33469

[51] Int. Cl.$^2$ .......................................... C07D 277/20
[52] U.S. Cl. ................... 424/270; 424/272; 546/275; 546/280; 548/187; 548/228
[58] Field of Search ............. 260/302 R, 307 R; 424/270, 272

[56] References Cited
U.S. PATENT DOCUMENTS

| 2,500,142 | 3/1950 | Wiesehahn | 206/302 |
| 4,012,412 | 3/1977 | Yamanaka et al. | 260/307 R |
| 4,053,478 | 10/1977 | Yamanaka et al. | 260/295 R |

FOREIGN PATENT DOCUMENTS

43383/71 12/1971 Japan .
77061/77 6/1977 Japan .
7669/78 1/1978 Japan .
1501588 2/1978 United Kingdom .

OTHER PUBLICATIONS

JACS, vol. 72 (713138-3140 (1950).
CA, 44 7174-g (1950).
JCS, 4099-4106 (1952).

Primary Examiner—Nicholas S. Rizzo
Attorney, Agent, or Firm—Sughrue, Rothwell, Mion, Zinn and Macpeak

[57] ABSTRACT

Oxazole- and thiazole-alkanoic acid compounds useful as drugs for the treatment of atherosclerosis with lipid metabolism disorder, and having the formula:

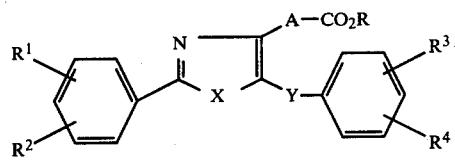

wherein R is a hydrogen atom, an alkyl group having 1 to 4 carbon atoms, an aralkyl group, a pyridylmethyl group or a tocopheryl group; each of $R^1$ and $R^2$ is a hydrogen atom or a halogen atom; $R^3$ is a hydrogen atom, a halogen atom or an alkyl group having 1 to 4 carbon atoms; $R^4$ is a hydrogen atom, a halogen atom, a nitro group, an alkyl group having 1 to 4 carbon atoms, an alkoxy group having 1 to 4 carbon atoms or a trifuloromethyl group; each of X and Y is an oxygen atom or a sulfur atom; and A is a straight or branched alkylene group having 1 to 4 carbon atoms, and pharmaceutically acceptable salts thereof are disclosed.

9 Claims, No Drawings

OXAZOLE- AND THIAZOLE-ALKANOIC ACID COMPOUNDS

This invention relates to novel and therapeutically valuable oxazole- and thiazole-alkanoic acid compounds of the formula:

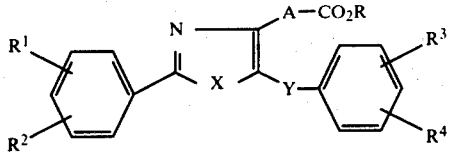
(I)

and pharmaceutically acceptable salts thereof, wherein:
R is a hydrogen atom, an alkyl group having 1 to 4 carbon atoms (e.g. methyl, ethyl, propyl or butyl), an aralkyl group (e.g. benzyl or phenethyl), a pyridylmethyl group (e.g. 3-pyridylmethyl) or a tocopheryl group;
each of $R^1$ and $R^2$ is a hydrogen atom or a halogen atom (fluorine, chlorine, bromine or iodine);
$R^3$ is a hydrogen atom, a halogen atom (fluorine, chlorine, bromine or iodine) or an alkyl group having 1 to 4 carbon atoms (e.g. methyl, ethyl, propyl or butyl);
$R^4$ is a hydrogen atom, a halogen atom (fluorine, chlorine, bromine or iodine), a nitro group, an alkyl group having 1 to 4 carbon atoms (e.g. methyl, ethyl, propyl or butyl), an alkoxy group having 1 to 4 carbon atoms (e.g. methoxy, ethoxy, propoxy or butoxy) or a trifluoromethyl group;
each of X and Y is an oxygen atom or a sulfur atom; and
A is a straight or branched alkylene group having 1 to 4 carbon atoms (e.g. methylene, ethylene, trimethylene, methylmethylene, dimethylmethylene or dimethylethylene).

Preferable compounds of the formula (I) are those wherein R is a hydrogen atom, an alkyl group having 1 to 4 carbon atoms, a pyridylmethyl group or a tocopheryl group, each of $R^1$ and $R^2$ is a hydrogen atom or a halogen atom, each of $R^3$ and $R^4$ is a hydrogen atom, a halogen atom or an alkyl group having 1 to 4 carbon atoms, each of X and Y is an oxygen atom or a sulfur atom, and A is a methylene group.

More preferable compounds of the formula (I) are those wherein R is a hydrogen atom or an alkyl group having 1 to 4 carbon atoms, $R^1$ is a chlorine atom, $R^2$ is a hydrogen atom, $R^3$ is a hydrogen atom or a chlorine atom and $R^4$ is a hydrogen atom or $R^3$ is a methyl group and $R^4$ is a hydrogen atom or a methyl group, both X and Y are an oxygen atom or a sulfur atom, and A is a methylene group.

This invention further relates to a method of preparing the compounds of formula (I) and a pharmaceutical composition containing the same.

The compounds of formula (I) can be prepared according to one of the following methods (a) to (c):

(a) In the case of compounds of formula (I) wherein R is an alkyl group having 1 to 4 carbon atoms, an aralkyl group or a pyridylmethyl group, by dehydrating a compound of the formula:

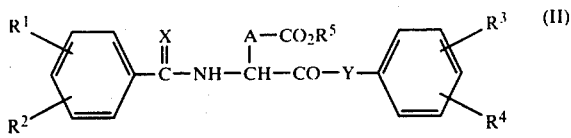
(II)

wherein $R^5$ is an alkyl group having 1 to 4 carbon atoms, an aralkyl group or a pyridylmethyl group and other symbols are as defined above.

The dehydration is carried out by treating the compound of formula (II) with a dehydrating agent (e.g. phosphorus pentoxide, phosphorus pentachloride, phosphorus oxychloride, phosphorus trichloride, thionyl chloride, tosyl chloride, phosphorus pentasulfide or concentrated sulfuric acid) with or without a solvent (e.g. benzene, toluene, chloroform, ligroin or 1,2-dichloroethane) at room temperature or under heating.

(b) In the case of compounds of formula (I) wherein R is a hydrogen atom by hydrolyzing a compound of the formula:

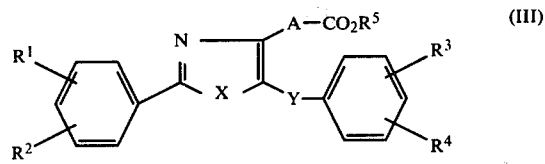
(III)

wherein each symbol is as defined above.

The hydrolysis is carried out by treating the compound of formula (III) with an acid or an alkali, preferably with an alkali hydroxide such as sodium hydroxide or potassium hydroxide, in a solvent such as water, an alcohol (e.g. methanol or ethanol), a ketone (e.g. acetone or methyl ethyl ketone), a water-miscible ether (e.g. dioxane or tetrahydrofuran) or a mixture thereof.

(c) In the case of compounds of formula (I) wherein R is an alkyl group having 1 to 4 carbon atoms, an aralkyl group, a pyridylmethyl group or a tocopheryl group, by reacting a compound of the formula:

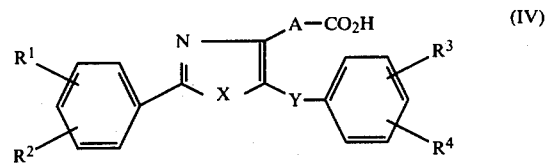
(IV)

wherein each symbol is as defined above, a salt thereof or a functional derivative thereof with a compound of the formula:

$R^6-Z$ (V)

wherein $R^6$ is an alkyl group having 1 to 4 carbon atoms, an aralkyl group, a pyridylmethyl group or a tocopheryl group and Z is a hydroxy group, a halogen atom (e.g. chlorine, bromine or iodine), an alkyl- or aryl-sulfonyloxy group (e.g. mesyl or tosyl) or a group of an alkyl sulfonate (e.g. —$OSO_2OCH_3$).

The functional derivative of the compound of formula (IV) is, for example, an acid halide (e.g. acid chloride or acid bromide), an acid anhydride, a mixed acid anhydride formed by reacting an acid of the formula (IV) with an alkyl chloroformate having 1 to 4 carbon atoms in the alkyl group or an inorganic halogen compound (e.g. phosphorus oxychloride, phosphorus trichloride or thionyl chloride), an acid azide or a reactive ester (e.g. p-nitrophenyl ester, N-hydroxysuccinimide ester or a polychlorophenyl ester).

Esterification is carried out by heating the compound of formula (IV) with an excess amount of an alcohol corresponding to the compound of formula (V) in the presence of an inorganic acid (e.g. hydrochloric acid or sulfuric acid) or by dehydrating without catalyst.

O-Alkylation is carried out in a solvent (e.g. acetone, methyl ethyl ketone, tetrahydrofuran, dimethylformamide or dimethylsulfoxide) in the presence of an acid acceptor (e.g. sodium carbonate, potassium carbonate, sodium hydrogen carbonate, pyridine or triethylamine) under heating or at room temperature.

In the case of the reaction of the functional derivative of the compound of formula (IV) with the alcohol of formula (V), the reaction is usually carried out with or without a solvent (e.g. benzene, ether, chloroform or dimethylformamide) at an appropriate temperature, if necessary, in the presence of an acid acceptor.

The compounds of formula (I) can, if desired, be converted in a conventional manner into a corresponding metal (e.g. sodium, potassium, calcium, magnesium or aluminum) salt, ammonium salt, an addition salt of an organic or inorganic acid (e.g. fumaric, maleic, hydrochloric or sulfuric acid), organic base (e.g. dimethylamine or triethylamine) or amino acid (e.g. arginine or lysine).

The starting compounds of formula (II) can, for example, be prepared as follows:

(i) In the case of compounds of formula (II) wherein X is an oxygen atom and other symbols are as defined above, by reacting a compound of the formula:

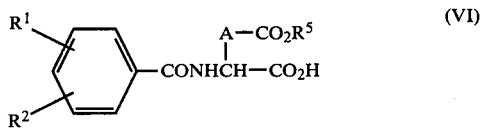

wherein each symbol is as defined above, a salt thereof or a functional derivative thereof with a compound of the formula:

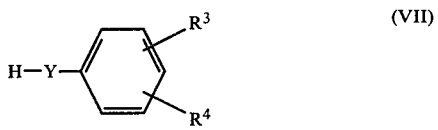

wherein each symbol is as defined above.

(ii) In the case of compounds formula (II) wherein X is a sulfur atom and other symbols are as defined above, by converting a compound of the formula (II) wherein X is an oxygen atom and other symbols are as defined above, into a thioamide derivative of the formula:

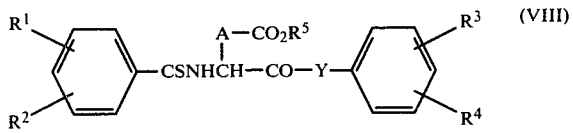

wherein each symbol is as defined above.

This conversion is preferably carried out with phosphorus pentasulfide with or without a solvent (e.g. chloroform, 1,2-dichloroethane, benzene, toluene, xylene, tetralin, tetrahydrofuran or dioxane) under heating or at room temperature. Thioamide compounds of formula (VIII) are ordinarily used in a subsequent reaction without isolation and purification.

The compounds of formula (II) may have L-, D- or DL-configuration in an α-carbon atom.

Specific examples of the preparation of the starting compounds (II):

(a) β-Methyl-α-p-chlorophenyl N-p-chlorobenzoyl-L-aspartate

To a stirred solution of 133 g of β-methyl N-p-chlorobenzoyl-L-aspartate in a crude semisolid (synthesized by reacting β-methyl L-aspartate with p-chlorobenzoyl chloride) and 62 g of p-chlorophenol in 500 ml of dimethylformamide at room temperature, 101 g of N,N'-dicyclohexylcardodiimide was added. The whole mixture was further stirred overnight. The precipitated N,N'-dicyclohexylurea was filtered off, and to the filtrate were added 3 l of water and 800 ml of ethyl acetate. After the mixture was shaken, the organic layer was washed twice with an aqueous sodium chloride, dried over anhydrous sodium sulfate and concentrated. Recrystallization of the residue from a mixture of n-hexane and ethyl acetate gave 85 g of the title compound, melting at 115°-116° C.

(b) β-Ethyl-α-thiophenyl N-p-chlorobenzoyl-L-aspartate

To a stirred solution of 30 g of β-ethyl N-p-chlorobenzoyl-L-aspartate (synthesized by reacting β-ethyl L-aspartate with p-chlorobenzoyl chloride) and 11 g of thiophenol in 250 ml of ethyl acetate with cooling in an ice-bath was added 21 g of N,N'-dicyclohexylcarbodiimide. After the whole mixture was further stirred at room temperature for 3 hours, the precipitated N,N'-dicyclohexylurea was filtered off and the solvent was evaporated from the filtrate. To the crystalline precipitate was added ethanol and the precipitate was filtered off. Recrystallization from ethanol gave 32 g of the title compound, melting at 95°-96° C.

The compounds of formula (I) possess excellent hypolipidemic activity and very low toxicity, as shown, by the following experiments, and are useful as drugs for the treatment of atherosclerosis with lipid metabolism disorder.

Hypolipidemic Action (1) Male rats with normolipidemia:

Male Wistar rats (170–250 g) were used. Each group was composed of 6 animals. The test compound was orally given by a gastric tube for 5 days. Cholesterol and triglyceride in the serum were determined by the standard methods using antoanalyzer (Technicon Inc.). The levels in the control group were considered as 100% and the reduction rate (%) in the test group was calculated. The results are shown in Table 1.

(2) Male mice with hyperlipidemia:

Male dd-strain mice (20–25 g) were used. Each group was composed of 10 animals. Mice were fed a high cholesterol diet (1% cholesterol, 0.2% sodium cholate, 5% olive oil and 93.8% commercial diet) for 5 days. The test compound was orally administered to the animals once a day throughout the experimental period. The serum cholesterol was determined by the procedure described in Experiment (1). The results are shown in Table 2.

Acute Toxicity

Male dd-strain mice (20–25 g) were used. Each group was composed of 10 animals. The test compound was orally administered to the animals. The $LD_{50}$ (mg/kg) was calculated from the mortality within 7 days after administration of the test compound. The results are shown in Table 3.

Serum Levels in Rhesus Monkey

The test compound was orally administered to rhesus monkeys at the dose of 10 mg/kg. Blood was collected at 0, 2, 4, 6, 8, 24, 30 and 48 hours after the administration of the test compound. After centrifugation, serum was stored at $-20°$ C. until taken for analysis. Serum drug was extracted with ethyl acetate and fluorometrically determined.

Results

Test Compounds:
A: Ethyl 2-p-chlorophenyl-5-p-chlorophenoxy-4-oxazoleacetate
B: 2-p-Chlorophenyl-5-phenoxy-4-oxazoleacetic acid monohydrate
C: Ethyl 2-p-chlorophenyl-5-phenylthio-4-thiazoleacetate
D: Ethyl 2-p-chlorophenyl-5-ethoxy-4-oxazoleacetate.
(for comparison, prior art compound disclosed in the U.S. Pat. No. 4,012,412)
Clofiblate (for comparison)

Table 1

| Compound | Dose (mg/kg/day) | Decrease (%) Cholesterol | Decrease (%) Triglyceride | Increase (%) Liver Weight |
|---|---|---|---|---|
| A | 100 | 40* | 33* | 5 |
| B | 100 | 37* | 33* | −6 |
| C | 100 | 40* | 29* | 15 |
| D | 100 | 32* | 33* | 5 |
| Clofibrate | 100 | 32* | 34* | 17* |

(*: $p < 0.05$)

Table 2

| Compound | Dose (mg/kg/day) | Decrease (%) of Serum Cholesterol |
|---|---|---|
| A | 100 | 37* |
| B | 100 | 38* |
| C | 100 | 34* |
| D | 100 | 37* |
| Clofibrate | 100 | 16 |

( * : $p < 0.05$)

Table 3

| Compound | $LD_{50}$(mg/kg, p.o.) (mice) |
|---|---|
| A | >6,000 |
| D | 3,700 |
| Clofibrate | 1,500 |

Table 4

| Compound | Peak level (μg/ml) | Half-life (hr) |
|---|---|---|
| A | 30 | 30 |
| D | 15 | 3 |

(Wavelengths for fluorometric determination: excitation: 294 nm, emission: 365 nm with compound A; excitation: 305 nm, emission: 370 nm with compound D)

From the data of Table 1, the hypolipidemic activity of the compounds of the present invention is estimated to be somewhat greater than that of the prior art compound D and clofibrate. Clofibrate has induced a significant liver enlargement at a dose of 100 mg/kg, but the compounds of the present invention, for example, compound A has shown no hepatomegaly even at a high dose of 500 mg/kg.

From the data of Table 3, it is shown that the compounds of the present invention have very low toxicity.

From the data of Table 4, serum levels of the compounds of the present invention have been higher and persisted longer than those of the prior art compound D in monkey, in which the pharmacokinetics of the compound D had been turned out to be similar to that of human beings. The compounds of the present invention would, therefore, be expected to be more active at a small dose in humankind.

In view of the experiments including those mentioned above, the compounds (I) of the present invention can be administered safely as drugs for the treatment of atherosclerosis with lipid metabolism disorder, in the form of a pharmaceutical preparation with a suitable and conventional carrier or adjuvant, administered orally, without harmful side effects to the patients.

The oral daily dose of the compounds (I) of the present invention for human adults usually ranges from 100 to 1,000 milligrams.

FORMULATION EXAMPLE 100 mg tablets are prepared from the following compositions:

| | |
|---|---|
| Compound A | 100.0 mg |
| Lactose | 60.0 mg |
| Microcrystalline cellulose | 20.0 mg |
| Starch | 23.3 mg |
| Methyl cellulose | 1.0 mg |
| Talc | 5.0 mg |
| Magnesium stearate | 0.7 mg |
| | 210.0 mg |

The present invention will be better understood from the following examles, which are merely intended to be illustrative and not limitative of the present invention.

EXAMPLE 1

2-p-Chlorophenyl-5-p-chlorophenoxy-4-oxazoleacetic acid (a) A solution of 85 g of β-methyl-α-p-chlorophenyl N-p-chlorobenzoyl-L-aspartate in 400 ml of phosphorus oxychloride was refluxed under heating for about 80 minutes. After cooling, the excess amount of phosphorus oxychloride was evaporated under reduced pressure. To the residue were added ice-cold water and potassium carbonate, and the resulting solution was extracted with ethyl acetate. The organic layer was washed with diluted potassium carbonate and water, dried over anhydrous sodium sulfate, and then concentrated to give 80 g of crude methyl 2-p-chlorophenyl-5-p-chlorophenoxy-4-oxazoleacetate as a pale brown oil.

(b) To a solution of 80 g of the above methyl ester product in 400 ml of acetone was added portionwise a 100 ml aqueous solution of 11.5 g of sodium hydroxide with cooling in an ice-bath. The mixture was stirred at room temperature for 180 minutes. The solvent was distilled off under reduced pressure. After ice was added to the residue, the mixture was acidified with hydrochloric acid to precipitate the objective carboxylic acid as a white solid.

The solid was filtered off, washed with water, dried and recrystallized from a mixture of ethyl acetate and ethanol to give 57 g of the purified title compound as a white fine powder, melting at 190°–192° C.

The following compounds can be prepared in a similar manner as Example 1a:
  Methyl 2-p-chlorophenyl-5-m-nitrophenoxy-4-oxazoleacetate, melting at 99°–101° C. (recrystallized from a mixture of n-hexane and ethyl acetate);
  Methyl 2-p-chlorophenyl-5-(2,4-dichlorophenoxy)-4-oxazoleacetate, melting at 134°–135° C. (recrystallized from methanol);
  Methyl 2-(3,4-dichlorophenyl)-5-p-chlorophenoxy-4-oxazoleacetate, melting at 131°–132° C. (recrystallized from a mixture of methanol and acetone).

The following compounds can be prepared in a similar manner as Example 1b:
  2-Phenyl-5-phenoxy-4-oxazoleacetic acid, melting at 109°–110° C. (recrystallized from aqueous ethanol);
  2-Phenyl-5-p-chlorophenoxy-4-oxazoleacetic acid, melting at 136°–137° C. (recrystallized from aqueous ethanol);
  2-p-Chlorophenyl-5-phenoxy-4-oxazoleacetic acid monohydrate, melting at 138°–141° C. (recrystallized from ethyl acetate);
  2-p-Chlorophenyl-5-m-nitrophenoxy-4-oxazoleacetic acid, melting at 167°–169° C. (recrystallized from a mixture of n-hexane and ethyl acetate);
  2-p-Chlorophenyl-5-m-trifluoromethylphenoxy-4-oxazoleacetic acid, melting at 174°–175° C. (recrystallized from ethyl acetate);
  2-p-Chlorophenyl-5-(2,4-dichlorophenoxy)-4-oxazoleacetic acid, melting at 174°–175° C. (recrystallized from a mixture of n-hexane and ethyl acetate);
  3-(2-p-Chlorophenyl-5-phenoxy-4-oxazole)propionic acid, melting at 102°–104° C. (recrystallized from aqueous ethanol);
  3-(2-p-Chlorophenyl-5-p-chlorophenoxy-4-oxazole)propionic acid, melting at 127°–128° C. (recrystallized from methanol);
  2-(2-p-Chlorophenyl-5-p-chlorophenoxy-4-oxazole)propionic acid, melting at 123°–126° C. (recrystallized from 2-propanol);
  2-(3,4-Dichlorophenyl)-5-p-chlorophenoxy-4-oxazoleacetic acid, melting at 178.5°–180° C. (recrystallized from methanol).

EXAMPLE 2

Ethyl 2-p-chlorophenyl-5-p-chlorophenoxy-4-oxazoleacetate

To a solution of 33.3 g of 2-p-chlorophenyl-5-p-chlorophenoxy-4-oxazoleacetic acid in 100 ml of dimethylformamide were added 40 ml of ethyl bromide and 40 ml of triethylamine. The mixture was stirred at room temperature for 40 minutes and then allowed to stand overnight. To the resulting mixture were added water and ethyl acetate and then the mixture was shaken. The organic layer was washed successively with water, diluted hydrochloric acid and water, then dried over anhydrous sodium sulfate and concentrated under reduced pressure. The residue was recrystallized from a mixture of n-hexane and ethyl acetate to give 34.3 g of the title compound as white crystals, melting at 70°–72° C.

The following esters can be prepared in a similar manner as Example 2:
  Ethyl 2-p-chlorophenyl-5-phenoxy-4-oxazoleacetate, melting at 61°–63° C. (recrystallized from n-hexane);
  Ethyl 2-p-chlorophenyl-5-m-nitrophenoxy-4-oxazoleacetate, melting at 128°–130° C. (recrystallized from a mixture of n-hexane and ethyl acetate);
  Ethyl 2-p-chlorophenyl-5-m-trifluoromethylphenoxy-4-oxazoleacetate, melting at 55°–58° C. (recrystallized from a mixture of n-hexane and ethyl acetate);
  Ethyl 2-p-chlorophenyl-5-(2,4-dichlorophenoxy)-4-oxazoleacetate, melting at 150°–151° C. (recrystallized from ethyl acetate);
  Ethyl 3-(2-p-chlorophenyl-5-phenoxy-4-oxazole)propionate, oil, $n_D^{23}=1.5635$;
  Ethyl 3-(2-p-chlorophenyl-5-p-chlorophenoxy-4-oxazole)propionate, melting at 54°–56° C. (recrystallized from n-hexane);
  Benzyl 2-p-chlorophenyl-5-p-chlorophenoxy-4-oxazoleacetate, melting at 68°–70° C. (recrystallized from n-hexane);
  3-Pyridylmethyl 2-p-chlorophenyl-5-p-chlorophenoxy-4-oxazoleacetate, melting at 82°–84° C. (recrystallized from aqueous ethanol); hydrochloride melts at 184°–185° C. (recrystallized from a mixture of isopropyl ether and methanol).

EXAMPLE 3

Methyl 2-p-chlorophenyl-5-m-nitrophenoxy-4-oxazoleacetate (1) To a solution of 1.0 g of 2-p-chlorophenyl-5-m-nitrophenoxy-4-oxazoleacetic acid in 20 ml of methanol was added 0.02 ml of concentrated sulfuric acid. The mixture was refluxed under heating for 45 minutes on a mantle heater. After the completion of reaction, the solvent was distilled off under reduced pressure. To the residue were added ice-cold water and potassium carbonate, and the mixture was extracted with ethyl acetate. After the organic layer was concentrated, recrystallization of the residue from a mixture of n-hexane and ethyl acetate gave 0.97 g of the title compound, melting at 97°–99° C.

(2) A solution of 1.5 g of 2-p-chlorophenyl-5-m-nitrophenoxy-4-oxazoleacetic acid in 8.5 ml of thionyl chloride was refluxed under heating for 20 minutes. The excess thionyl chloride was distilled off under reduced pressure and to the residue was added 20 ml of methanol. After the mixture was shaken at room temperature for about 15 minutes and cooled in an ice-bath, the precipitate was filtered off, dried and recrystallized from a mixture of n-hexane and ethyl acetate to give 1.0 g of the title compound, melting at 98°–100° C.

EXAMPLE 4

Methyl 2-p-chlorophenyl-5-(2,5-dimethylphenoxy)-4-oxazoleacetate

To a stirred solution of 46.4 g of β-methyl N-p-chlorobenzoyl-L-aspartate and 39.1 g of 2,5-dimethylphenol in 300 ml of ethyl acetate was added 33.0 g of N,N'-dicyclohexylcarbodiimide. The mixture was further stirred for several hours and allowed to stand overnight. The N,N'-dicyclohexylurea precipitated was filtered off, and the filtrate was concentrated under reduced pressure. The residue was evaporated under reduced pressure and a forerun collected to 86° C. in a pressure of 5 mmHg was removed to give 66.7 g of crude β-methyl-α-2,5-dimethylphenyl N-p-chlorobenzoyl-L-aspartate as a pale yellow oil. To a solution of 10 g of the crude ester product in 100 ml of toluene was added 10 ml of phosphorus oxychloride. The mixture was refluxed under heating for 5 hours and then cooled. The resulting mixture was poured into a mixture of ice and sodium carbonate and stirred. After shaking, the toluene layer was washed with sodium carbonate and water, dried over anhydrous sodium sulfate and concentrated under reduced pressure. Residual crystals were recrystallized from methanol to give 4.06 g of the title compound as colorless needles, melting at 113° C.

The following compounds can be prepared in an identical manner as Example 4:
  Methyl 2-p-chlorophenyl-5-p-methylphenoxy-4-oxazoleacetate, melting at 76° C. (recrystallized from methanol);
  Methyl 2-p-chlorophenyl-5-p-methoxyphenoxy-4-oxazoleacetate, melting at 73°–74° C. (recrystallized from methanol).

EXAMPLE 5

2-p-Chlorophenyl-5-(2,5-dimethylphenoxy)-4-oxazoleacetic acid

To a stirred solution of 13 g of methyl 2-p-chlorophenyl-5-(2,5-dimethylphenoxy)-4-oxazoleacetate prepared in Example 4 in 150 ml of acetone at room temperature was dropwise added a 15 ml aqueous solution of 2.0 g of sodium hydroxide. The mixture was further stirred for 3.5 hours. After the solvent was evaporated under reduced pressure, water was added to the remaining aqueous solution. The resulting solution was cooled and acidified to pH 3 with hydrochloric acid. The crystalline precipitate was filtered off and recrystallized from ethanol to give 9.05 g of the title compound as bulky needles, melting at 185° C.

The following acids can be prepared in an identical manner as Example 5:
  2-p-Chlorophenyl-5-p-methylphenoxy-4-oxazoleacetic acid, melting at 183° C. (recrystallized from ethanol);
  2-p-Chlorophenyl-5-p-methoxyphenoxy-4-oxazoleacetic acid, melting at 145°–146° C. (recrystallized from ethanol).

EXAMPLE 6

Ethyl 2-p-chlorophenyl-5-(2,5-dimethylphenoxy)-4-oxazoleacetate

To a solution of 0.80 g of 2-p-chlorophenyl-5-(2,5-dimethylphenoxy)-4-oxazoleacetic acid in 8 ml of dimethylformamide were added 1 ml of triethylamine and 1.5 ml of ethyl bromide. The mixture was stirred at 35°–40° C. for 90 minutes. The reaction mixture was poured into water and ethyl acetate and shaken with a separate funnel. The organic layer was successively washed with water, diluted hydrochloric acid and water, dried over anhydrous sodium sulfate and concentrated under reduced pressure. The white crystalline residue was recrystallized from n-hexane to give 0.68 g of the title compound as white fine needles, melting at 122°–123.5° C.

EXAMPLE 7

Ethyl 2-p-chlorophenyl-5-phenylthio-4-oxazoleacetate

To a solution of 3.9 g of β-ethyl-α-thiophenyl p-chlorobenzoyl-L-aspartate in 40 ml of toluene was added 30 ml of phosphorus oxychloride, and the mixture was refluxed under heating for 4 hours. After cooling, aqueous sodium hydrogen carbonate was added to the mixture and the resulting mixture was extracted with ethyl acetate. The extract was washed with water, dried over anhydrous sodium sulfate and the solvent was distilled off. Recrystallization of the residue from ethanol gave 3.0 g of the title compound, melting at 109°–110° C.

The following compound can be prepared in an identical manner as Example 7:
  Ethyl 2-p-chlorophenyl-5-p-chlorophenylthio-4-oxazoleacetate, melting at 101°–103° C. (recrystallized from ethanol).

EXAMPLE 8

Ethyl 2-p-chlorophenyl-5-phenylthio-4-thiazoleacetate

To a solution of 16.5 g of β-ethyl-α-thiophenyl p-chlorobenzoyl-L-aspartate in 160 ml of 1,2-dichloroethane was added 9 g of phosphorus pentasulfide. The mixture was refluxed under heating with stirring for 1.5 hours. The reaction mixture was concentrated under reduced pressure and to the residue was added aqueous sodium hydrogen carbonate. The mixture was extracted with ethyl acetate, and the extract was washed with water and dried over anhydrous sodium sulfate, and then the solvent was evaporated. Recrystallization of the crystalline residue from ethanol gave 9.2 g of the title compound, melting at 71°–73° C.

The following compound can be prepared in an identical manner as Example 8.
  Ethyl 2-p-chlorophenyl-5-p-chlorophenylthio-4-thiazoleacetate, melting at 104°–105° C. (recrystallized from ethanol).

EXAMPLE 9

2-p-Chlorophenyl-5-phenylthio-4-thiazoleacetic acid

To a solution of 3.4 g of ethyl 2-p-chlorophenyl-5-phenylthio-4-thiazoleacetate in 100 ml of methanol was added 15 ml of 3 N aqueous potassium hydroxide. The mixture was stirred at room temperature for 3 hours. The solvent was distilled off under reduced pressure and water was added to the residue. The solution was acidified with hydrochloric acid. The white precipitated solid was filtered off, washed with water, dried and recrystallized from ethanol to give 2.3 g of the title compound, melting at 191°–193° C.

The following compounds can be prepared in an identical manner as Example 9:
  2-p-Chlorophenyl-5-p-chlorophenylthio-4-thiazoleacetic acid, melting at 200°–202° C. (recrystallized from ethanol);
  2-p-Chlorophenyl-5-phenylthio-4-oxazoleacetic acid, melting at 174°–175° C. (recrystallized from ethanol);
  2-p-Chlorophenyl-5-p-chlorophenylthio-4-oxazoleacetic acid, melting at 212°–213° C. (recrystallized from ethanol);

2-p-Chlorophenyl-5-p-chlorophenoxy-4-thiazoleacetic acid, melting at 170° C. (recrystallized from a mixture of ethanol and n-hexane);

2-p-Chlorophenyl-5-p-methoxyphenoxy-4-thiazoleacetic acid, melting at 145°-146° C. (recrystallized from ethanol);

2-p-Chlorophenyl-5-(2,5-dimethylphenoxy)-4-thiazoleacetic acid, melting at 163°-164° C. (recrystallized from a mixture of ethanol and n-hexane).

EXAMPLE 10

Ethyl 2-p-chlorophenyl-5-phenylthio-4-oxazoleacetate

To a solution of 3.6 g of 2-p-chlorophenyl-5-phenylthio-4-oxazoleacetic acid in 10 ml of dimethylformamide were added 4 ml of ethyl bromide and 4 ml of triethylamine. The mixture was stirred at room temperature for 4 hours. To the reaction mixture were added water and ethyl acetate and the resulting mixture was shaken. The organic layer was successively washed with water, diluted hydrochloric acid and water, dried over anhydrous sodium sulfate and concentrated under reduced pressure. Recrystallization of the residue from ethanol gave 3.2 g of the title compound, melting at 109°-110° C.

EXAMPLE 11

Ethyl 2-p-chlorophenyl-5-p-chlorophenylthio-4-thiazoleacetate

To 1.0 g of 2-p-chlorophenyl-5-p-chlorophenylthio-4-thiazoleacetic acid were added 10 ml of benzene and 2.0 ml of thionyl chloride, and the mixture was refluxed for 30 minutes. The solvent and the excess thionyl chloride were distilled off under reduced pressure. To the residue was added 20 ml of ethanol and stirred at room temperature for 1 hour and then the solvent was distilled off under reduced pressure. Recrystallization of the residue from ethanol gave 0.8 g of the title compound, melting at 103°-104° C.

EXAMPLE 12 dl-α-Tocopheryl 2-p-chlorophenyl-5-p-chlorophenoxy-4-oxazoleacetate

A mixture of 1.82 g of 2-p-chlorophenyl-5-p-chlorophenoxy-4-oxazoleacetic acid and 20 ml of thionyl chloride was refluxed under heating for 3 hours. The excess thionyl chloride was distilled off. To a solution of the crude acid chloride thus obtained in 40 ml of benzene were added 2.15 g of dl-α-tocopherol and 3.5 ml of pyridine, and stirred at room temperature for 3 hours. The reaction mixture was poured into water, the benzene layer was successively washed with diluted hydrochloric acid, diluted aqueous sodium carbonate and water, and then concentrated. The residual oil was chromatographed on a column of silica gel (Merck silica gel 60) with a mixture of n-hexane and ethyl acetate (18.5:1.5). Fractions fluorescing on exposure of ultraviolet light of wavelengths 253.6 nm and 365 nm on a thin-layer plate were collected. Removal of the solvent gave 0.95 g of the title compound as a pale yellow and very viscous oil. $n_D^{22} = 1.550$; This compound showed one spot on a thin-layer chromatogram on silica gel in two different solvent systems, namely benzene and chloroform respectively.

What is claimed is:

1. A compound of the formula:

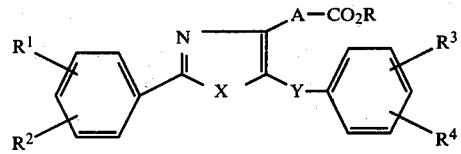

and pharmaceutically acceptable salts thereof, wherein:
   $R$ is a hydrogen atom or an ethyl group;
   $R^1$ is a chlorine atom at 4-position on the phenyl nucleus;
   $R^2$ is a hydrogen atom;
   $R^3$ is a hydrogen atom or a methyl group;
   $R^4$ is a hydrogen atom, a chlorine atom or a methyl group where $R^3$ is a hydrogen atom, or
   $R^4$ is a methyl group where $R^3$ is a methyl group;
   both X and Y are an oxygen atom or a sulfur atom; and
   A is a methylene group.

2. The compound of claim 1:
Ethyl 2-p-chlorophenyl-5-p-chlorophenoxy-4-oxazoleacetate.

3. The compound of claim 1:
Ethyl 2-p-chlorophenyl-5-phenoxy-4-oxazoleacetate.

4. The compound of claim 1:
2-p-Chlorophenyl-5-phenoxy-4-oxazoleacetic acid.

5. The compound of claim 1:
Ethyl 2-p-chlorophenyl-5-phenylthio-4-thiazoleacetate.

6. The compound of claim 1:
Ethyl 2-p-chlorophenyl-5-p-chlorophenylthio-4-thiazoleacetate.

7. The compound of claim 1:
2-p-Chlorophenyl-5-p-methylphenoxy-4-oxazoleacetic acid.

8. The compound of claim 1:
2-p-Chlorophenyl-5-(2,5-dimethylphenoxy)-4-oxazoleacetic acid.

9. A pharmaceutical composition comprising the compound of claim 1 in combination with a pharmaceutically acceptable inert carrier, said compound being present in a therapeutically effective amount.

* * * * *